US010071088B2

(12) United States Patent
Fleming

(10) Patent No.: US 10,071,088 B2
(45) Date of Patent: Sep. 11, 2018

(54) ANTI-NAUSEA DRUG COMBINATIONS

(71) Applicant: Precondit, LLC, Indianapolis, IN (US)

(72) Inventor: C. Andrew Fleming, Indianapolis, IN (US)

( * ) Notice: Subject to any disclaimer, the term of this patent is extended or adjusted under 35 U.S.C. 154(b) by 666 days.

(21) Appl. No.: 13/918,143

(22) Filed: Jun. 14, 2013

(65) Prior Publication Data

US 2013/0345250 A1 Dec. 26, 2013

Related U.S. Application Data

(60) Provisional application No. 61/664,622, filed on Jun. 26, 2012.

(51) Int. Cl.

| | |
|---|---|
| ***A61K 31/485*** | (2006.01) |
| ***A61K 31/167*** | (2006.01) |
| ***A61K 31/198*** | (2006.01) |
| ***A61K 31/27*** | (2006.01) |
| ***A61K 31/405*** | (2006.01) |
| ***A61K 31/465*** | (2006.01) |

(52) U.S. Cl.

CPC .......... *A61K 31/485* (2013.01); *A61K 31/167* (2013.01); *A61K 31/198* (2013.01); *A61K 31/27* (2013.01); *A61K 31/405* (2013.01); *A61K 31/465* (2013.01)

(58) Field of Classification Search

USPC .......................................................... 514/282

See application file for complete search history.

(56) References Cited

U.S. PATENT DOCUMENTS

| | | | |
|---|---|---|---|
| 5,985,874 A | 11/1999 | Owen et al. | |
| 6,197,329 B1 | 3/2001 | Hermelin et al. | |
| 8,124,126 B2 | 2/2012 | Bosse et al. | |
| 9,289,423 B2 | 3/2016 | Mouradian et al. | |
| 2002/0055544 A1 | 5/2002 | Kamin et al. | |
| 2005/0096311 A1 | 5/2005 | Suffin et al. | |
| 2006/0074101 A1 | 4/2006 | Baroni et al. | |
| 2007/0015728 A1 | 1/2007 | Ford | |
| 2009/0175939 A1 | 7/2009 | Bosse et al. | |
| 2011/0003005 A1* | 1/2011 | Venkatesh ............ | A61K 9/5073 424/494 |

FOREIGN PATENT DOCUMENTS

WO WO 2012/089738 A1 7/2012

OTHER PUBLICATIONS

Smarious (Pharmacology of rising oral doses of 5-hydroxytryptophan with carbidopa, J. Psychopharmacol, 2008, 22(4), pages 426-33.*

Fung (Drugs for Parkinson's disease, Australian Prescriber, vol. 24, No. 4, 2001.*

David (Norco Side Effects Center, 2015, pp. 1-5).*

Golebiewski (Prevention and treatment of postoperative nausea and vomiting, American Journal of Health-System Phamr, vol. 62, 2005, pp. 1247-1260).*

International Search Report and Written Opinion issued in PCT/US2013/045884, dated Oct. 16, 2013.

Andrews PL, Davis CJ, Bingham S, et al. The abdominal visceral innervation and the emetic reflex: pathways, pharmacology, and plasticity. Can J Physiol Pharmacol 1990; 68:324-345.

Apfel CC, Laara E, Koivuranta M, Greim CA, Roewer NA. Simplified Risk score for predicting postoperative nausea and vomiting: conclusions from cross-validations between two centers. Anesthesiology 1999;91:693-700.

Beattie WS, Lindblad T, Buckley DN, Forrest JB. Menstruation increases the risk of nausea and vomiting after laparoscopy. Anesthesiology 1993;78:272-6.

Bianchi, A. L.; et al. The Mechanisms and Control of Emesis. ISBN 0 86196 366 0 (0768-3154).

Carroll N, Miederhoff P, Cox F, Hirsch J. Costs incurred by outpatient surgical centers in managing postoperative nausea and vomiting. J. Clin. Anesth 1994;6:364-9.

Chimbira W, Sweeney BP. The effect of smoking on postoperative nausea and vomiting. Anaesthesia 2000;55:540-4.

Chung F, Mezei G. Factors contributing to a prolonged stay after ambulatory surgery. Anesth Analg 1999;89:1352-9.

Ionescu, D.; et al. Nicotine Patch for the Prevention of Postoperative Nausea and Vomiting: A Prospective Randomized Trial. Clin. Drug Investig.,2007;27(8);559-564.

Jones, J. M.; et al. Antiemetics for Chemotherapy-induced Nausea and Vomiting Occurring Despite Prophylactic Antiemetic Therapy. J. Palliat. Med.;2011;14(7);810-814.

Kasper S, Fuger J, Moller HJ. Comparative efficacy of antidepressants. Drugs. 1992;43 Suppl 2:11-22;discussion 22-3.

Kusnierczyk, NMA: et al. Outcomes of antiemetic prophylaxis in children undergoing bone marrow transplatation. Bone Marrow Transplatation 2002;30;119-124.

Lerman J. Surgical and patient factors involved in postoperative nausea and vomiting. Br J Anaesth 1992;69(Suppl 1):24S-32S.

Macario A, Weinger M, Carney S, Kim A. Which clinical anesthesia outcomes are important to avoid? The perspective of patients. Anesth Analg 1999;89:652-8.

Myles PS, Williams DL, Hendrata M, et al. Patient satisfaction after anaesthesia and surgery: results of a prospective survery of 10,811 patients. Br J Anaesth 2000;84:6-10.

Norred, C. L. Antiemetic prophylaxis: Pharmacology and therapeutics. AANA Journal, Apr. 2003;71(2);133-140.

Sweeney B P, Why does smoking protect against PONV? Br. J. Anaesth. Sweeney 89 (6): 810.

(Continued)

*Primary Examiner* — Kathrien A Cruz

(74) *Attorney, Agent, or Firm* — Woodard, Emhardt, Moriarty, McNett & Henry LLP

(57) ABSTRACT

Methods and compositions are disclosed for reducing Post Operative Nausea and/or Vomiting (PONV) in a human patient in need of general anesthesia. Such methods may include scheduling surgery for the human patient and administering to the patient one or more series of prescribed medicines days during a regimen preceding general anesthesia to condition receptors involved in the nausea and/or vomiting reflex.

1 Claim, No Drawings

(56) References Cited

OTHER PUBLICATIONS

Whalen F, Sprung J, Burkle C, et al. Recent smoking behavior and postoperative nausea and vomiting. Anesth Analg 2006;103:70-75.
Andrews PL, Sanger GJ. Abdominal vagal afferent neurons: an important target for the treatment of gastrointestinal dysfunction. Curr Opin Pharmacol. 2002;2:650-6.
Hinz, M. et al. Amino Acid management of Parkinson's disease: a case study International Journal of General Medicine, vol. 2011, No. 4 (2011), pp. 165-174.
Huang, Han-Yao et al. Impact of Pill Organizaers and Blister Packs on Adherence to Pill Taking in Two Vitamin Supplementation Trials American Journal of Epidemiology, vol. 152, No. 8 (2000), pp. 780-787.
Doyle, Case, "Novel Preconditioning Approach did not reduce Postoperative Nausea and Vomiting after General Anesthesia," Anesthesiology News (Nov. 27, 2017).

* cited by examiner

ANTI-NAUSEA DRUG COMBINATIONS

CROSS-REFERENCE TO RELATED APPLICATIONS

This application claims the benefit of priority from Provisional U.S. application Ser. No. 61/664,622, filed Jun. 26, 2012 which is hereby incorporated by reference in its entirety.

BACKGROUND OF INVENTION

Nausea and vomiting are common side effects of certain pharmacologic interventions and of surgery. These side effects can result from mechanical stimulation of the gastrointestinal tract, from chemical stimulation of various receptors in the body, or from both. These effects are particularly bothersome after surgical procedures under general anesthesia. Despite intense and ongoing efforts in past decades to reduce the impact of the problem, complete success remains elusive. A study in 1999 found the overall incidence of postoperative nausea and vomiting remained at a level of 30%, and rose even higher in the subset of patients with two or more risk factors.[i]

Patients' perception of the quality of their anesthetic experience is strongly affected by the incidence of postoperative nausea and vomiting (PONV).[ii] Patients have even shown a willingness to pay out of pocket to avoid the problem of PONV.[iii] There is also considerable economic impact on the facilities that treat these patients and may have to deal with additional staffing and overhead costs as a result of delayed patient discharge due to PONV.[iv v]

Various patient specific factors are known to influence the risk of nausea and vomiting. Some of the relevant factors influencing the risk of PONV include:

- Female gender
- Age
- Menstrual cycle
- History of motion sickness
- Previous history of PONV
- Smoking status
- Type of surgical procedure
- Types of anesthetic agents used Nausea and vomiting can be triggered by the introduction into the body of chemical substances or drugs, whether via oral or parenteral routes. These substances then result in activation of receptors in the brain or the proximal small intestine.[vi vii] If these introduced substances are interpreted by the brain as foreign or noxious, nausea and or emesis may ensue, as the human body perceives these drugs to be ingested foreign substances, which must be expelled from the body.

Most therapies introduced in the last few decades to combat drug-related nausea are intended to act at the receptor level by blocking receptors commonly believed to be involved in the reflex mediating a triggering of the emetic response. These therapies have included antihistamines, anticholinergic drugs, drugs acting on dopamine receptors, 5-HT3 receptor blockers, and more recently, an NK-1 receptor blocker, aprepitant.

The proposed invention utilizes a multi-component compound in a novel way. Rather than block key receptors immediately prior to or at the time of exposure to noxious agents, or immediately after symptoms of nausea and vomiting have appeared, this approach involves a conditioning approach whereby several of the principal known receptors in the nausea and vomiting reflex are gradually de-sensitized over a period of 7 or more days prior to the patient being exposed to the noxious agent(s). This desensitization is hypothesized to occur in two ways:

1. Agents similar in chemical composition or class to the drugs commonly used during the perioperative period are given in sub-emetic doses during this conditioning phase so as to desensitize the receptor groups to subsequent stimulation when similar drugs are given during the perioperative period. This is possible since humans can become tolerant to noxious substances upon repeated exposure.

2. Sub-therapeutic doses of some of the intermediate neurotransmitters involved in the nausea-vomiting arc are given such that desensitization and a reduced response will occur.

Mechanism #1 is analogous to the presumed mechanism by which smokers are protected from the nausea inducing effects of some drugs. Smokers constantly expose the chemoreceptor areas of their nervous system to a diverse blend of noxious chemical substances, which are introduced by inhalation and through the mucous membranes. They frequently experience nausea when they first begin to smoke cigarettes if they imbibe too much or too quickly. After a time, the smoker's body becomes desensitized to this wide variety of noxious agents. This desensitization carries over if the patients are exposed to other extrinsic chemicals, such as anesthetic drugs administered at the time of surgery, which explains why smokers have a significantly lower risk of PONV than do non-smokers.[viii ix x]

Further evidence that desensitization can be accomplished is seen with serotonergic drugs. Selective serotonin reuptake inhibitors (SSRIs) are a commonly administered class of drugs given to treat depression and other disorders. The most common side effect of all SSRI drugs is nausea, which is not surprising since these drugs raise the serum level of serotonin, which is known to function as a neurotransmitter in the nausea and vomiting reflex. Patients report anecdotally, however, that the nausea typically goes away after the first week or two of treatment and can be avoided or minimized by increasing the dosage slowly at the onset of treatment. This was also seen, particularly in early studies with SSRIs, where it was observed that gradual upward titration of SSRI dosage could greatly reduce or eliminate nausea symptoms when SSRI therapy was initiated.[xi]

By using the phased, gradual introduction of the emetic provoking drug, or an analog thereof, the reaction to the acute administration of the same or similar class drug may be reduced or eliminated. By exploiting these effects, this agent will have the potential to reduce the acute incidence of nausea and vomiting that results from a perioperative exposure.

The invention consists of a compound which contains agents designed to desensitize the subject, whether human or other animal, to a number of different drug classes, as well as non-specific agents designed to reduce the overall chemical sensitivity of the subject.

COMPOSITION OF INVENTION

The composition consists of a multi-component compound meant for oral ingestion. The components include:

1) Hydrocodone, chemical name 4,5a-Epoxy-3-methoxy-17-methylmorphinan-6-one tartrate (1:1) hydrate (2:5), chemical formula $C_{18}H_{21}NO_3$.

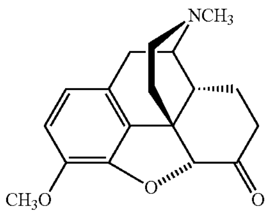

(public domain image)

The compound contains 2.5 mg. of hydrocodone per unit dose. Hydrocodone represents the opioid component of the compound.

2) 5-Hydroxytryptophan, chemical name 2-amino-3-(5-hydroxy-1H-indol-3-yl) propanoic acid, chemical formula $C_{11}H_{12}N_2O_3$.

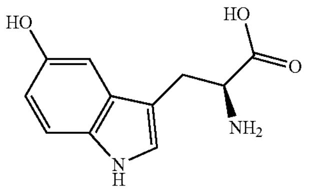

(public domain image)

The compound contains 50 mg. of 5-hydroxytryptophan per unit dose. 5-Hydroxytryptophan represents the serotonergic component of the compound.

3) Nicotine, chemical name (S)-3-(1-Methyl-2-pyrrolidinyl)pyridine, chemical formula $C_{10}H_{14}N_2$.

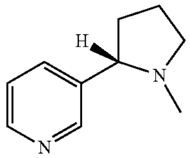

(public domain image)

The compound contains nicotine, 1-2 mg. per unit dose. Nicotine stimulates nicotinic acetylcholine receptors.

4) Bethanechol, chemical name 2-(carbamoyloxy)-N,N,N-trimethylpropan-1-aminium, chemical formula $C_7H_{17}N_2O_2$.

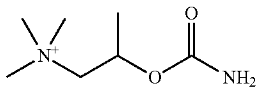

(public domain image)

The compound contains 2-5 mg. of bethanechol.

6) Levodopa, chemical name 3,4 dihydroxy-L-phenylalanine, L-3,4-dihydroxyphenylalanine, chemical formula $C_9H_{11}NO_4$.

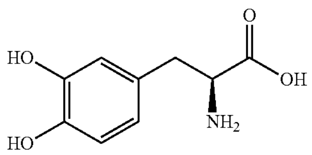

(public domain image)

The compound contains 50 mg. of L-DOPA, which stimulates the dopaminergic axis.

7) Inert matrix colorants, preservatives, and binders will ultimately be used in the production process.

For the purposes of the proposed invention, the compound comprises a combination of any or all of the ingredients disclosed herein. Thus, the compound can include, but is not limited to, a combination of one or more of the following ingredients: hydrocodone, 5-hydroxytryptophan, nicotine, bethanechol, levodopa, inert matrix colorants, preservatives, and binders.

In one embodiment of the invention, the following formulation is used:

1) Hydrocodone, chemical name 4,5a-Epoxy-3-methoxy-17-methylmorphinan-6-one tartrate (1:1) hydrate (2:5), chemical formula $C_{18}H_{21}NO_3$.

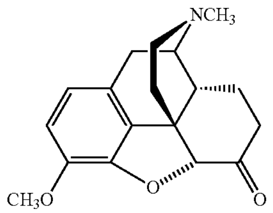

(public domain image)

The compound contains 2.5 mg. of hydrocodone per unit dose. Hydrocodone represents the opioid component of the compound.

2) 5-Hydroxytryptophan, chemical name 2-amino-3-(5-hydroxy-1H-indol-3-yl) propanoic acid, chemical formula $C_{11}H_{12}N_2O_3$.

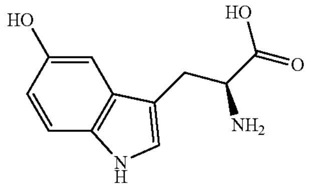

(public domain image)

The compound contains 50 mg. of 5-hydroxytryptophan per unit dose. 5-Hydroxytryptophan represents the serotonergic component of the compound.

3) Levodopa, chemical name 3,4 dihydroxy-L-phenylalanine, L-3,4-dihydroxyphenylalanine, chemical formula $C_9H_{11}NO_4$.

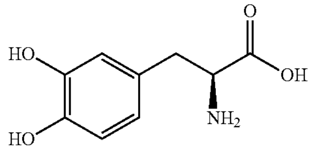

(public domain image)

The compound contains 50 mg. of L-DOPA, which stimulates the dopaminergic axis.

4) Inert matrix colorants, preservatives, and binders will ultimately be used in the production process.

Research Proposal Ver. 2.12.12

Can multiple axis stimulation of receptors involved in the human nausea and vomiting reflex be effectively pre-conditioned to reduce the incidence of post-operative nausea and vomiting?

Principal Investigator: C. Andrew Fleming, M.D.

SUMMARY

This is a prospective randomized experimental study to determine whether pre-conditioning three human receptor groups can reduce the magnitude of adverse effects, particularly nausea and vomiting, when the receptors are stimulated acutely by iatrogenic stimuli known to produce those adverse effects.

BACKGROUND

Nausea and vomiting are common side effects of certain pharmacologic interventions and of surgery. These side effects can result from mechanical stimulation of the gastrointestinal tract, from chemical stimulation of various receptors in the body, or from both. These effects are particularly bothersome after surgical procedures performed with general anesthesia. Despite intense and ongoing efforts in past decades to reduce the impact of the problem, complete success remains elusive. A study in 1999 found the overall incidence of postoperative nausea and vomiting remained at a level of 30%, and rose even higher in the subset of patients with two or more risk factors.[xii]

Patients' perception of the quality of their anesthetic experience is strongly affected by the incidence of postoperative nausea and vomiting (PONV).[xiii] Patients have even shown a willingness to pay out of pocket to avoid the problem of PONV.[xiv] There is also considerable economic impact on the facilities that treat these patients and may have to deal with additional staffing and overhead costs as a result of delayed patient discharge due to PONV.[xv xvi]

Various patient specific factors are thought to influence the risk of nausea and vomiting. Some of the relevant factors which may increase the risk of PONV include[xvii,xviii]:

Female gender
Age (inversely proportional)
Proximity to menstruation of female patients
History of motion sickness
Previous history of PONV
Non smoking status
Certain types of surgical procedures
Types of anesthetic agents used Nausea and vomiting can be triggered by the introduction into the body of chemical substances or drugs, whether via oral or parenteral routes. These substances then result in activation of receptors in the brain or the proximal small intestine.[xix xx] If these introduced substances are interpreted by the brain as foreign or noxious, nausea and or emesis may ensue, as the human body perceives these drugs to be ingested foreign substances, which must be expelled from the body.

Most therapies introduced in the last few decades to combat drug-related nausea are intended to act at the receptor level by blocking receptors commonly believed to be involved in the reflex mediating a triggering of the emetic response. These therapies have included antihistamines, anticholinergic drugs, drugs acting on dopamine receptors, 5-HT3 receptor blockers, and more recently, an NK-1 receptor blocker, aprepitant.

This study proposes to approach nausea and vomiting prophylaxis in a novel way. Rather than block key receptors immediately prior to or at the time of exposure to noxious agents, or immediately after symptoms of nausea and vomiting have appeared, this approach involves conditioning three of the principal known receptors in the nausea and vomiting reflex over a period of 14 days prior to the patient being exposed to the noxious agent(s). This desensitization is hypothesized to occur in two ways:

3. Agents similar in chemical composition or class to the drugs commonly used during the perioperative period are given in sub-emetic doses during this conditioning phase so as to desensitize the receptor groups to subsequent stimulation when similar drugs are given during the perioperative period. This desensitization is possible since humans can become tolerant to noxious substances upon repeated exposure.
4. Sub-therapeutic doses of some of the intermediate neurotransmitters involved in the nausea-vomiting arc are given such that desensitization and a reduced response will occur.

Method #1 is analogous to the presumed mechanism by which smokers are protected from the nausea inducing effects of some drugs. Smokers constantly expose the chemoreceptor areas of their nervous system to a diverse blend of noxious chemical substances, which are introduced by inhalation and through the mucous membranes. They frequently experience nausea when they first begin to smoke cigarettes if they imbibe too much or too quickly. After a certain amount of time, the smoker's body becomes desensitized to this wide variety of noxious agents. This desensitization carries over if the patients are exposed to other extrinsic chemicals, such as anesthetic drugs administered at the time of surgery, which explains why smokers have a significantly lower risk of PONV than do non-smokers.[xxi]

Further evidence that desensitization can be accomplished is seen with serotonergic drugs. Selective serotonin reuptake inhibitors (SSRIs) are a commonly administered class of drugs given to treat depression and other disorders. The most common side effect of all SSRI drugs is nausea, which is not surprising since these drugs raise the serum level of serotonin, which is known to function as a neurotransmitter in the nausea and vomiting reflex. Patients report anecdotally, however, that the nausea typically goes away after the first week or two of treatment and can be avoided or minimized by increasing the dosage slowly at the onset of treatment.

The proposed agents will be administered in such a way that the body desensitizes itself to substances which are identical or chemically related to those which would ordinarily trigger nausea and emesis when administered as part of a therapeutic intervention. By using the phased, gradual introduction of the emetic provoking drug, or an analog thereof, we hypothesize that the reaction to the acute administration of the same or similar class drug may be reduced or eliminated.

Overall Study Design:

Overview:

Three drugs, hydrocodone, 5-HTP, and L-DOPA, will be administered preoperatively over 10-14 days in gradually increasing dosages to the study treatment group (Group Y), which will consist of up to 125 patients who have met the screening criteria. A control group (Group X) of 125 similarly screened patients will receive a placebo medication over the same 10-14 day period. The study drug dosages will at all times be therapeutic or sub-therapeutic relative to typical clinical dosages of these drugs.

The patients will undergo scheduled operative procedures. Data will be collected on all aspects of the type of operative anesthetic administered, and the incidence of early (<6 hours post operatively) and late (6 to 24 hours) post operative nausea and vomiting. PONV data will be recorded using this scale:

0=no nausea or vomiting

1=nausea, but no vomiting

2=vomiting or retching

Statistical analysis of the resultant data will be performed to determine whether or not a statistically significant difference exists in the percentage of PONV between the treatment and the control groups.

Process:

1. Screening

Prospective enrollees will be recruited from the St. Vincent Womens Hospital clinic and general patient population of St. Vincent Womens Hospital or St. Vincent $86^{th}$ Street. Patients will complete a screening survey (attached) with their identifying, contact, and pertinent background medical information, including questions that will screen for patient inclusion/exclusion criteria. If not excluded, they will then complete an Inclusion/Exclusion checklist (attached). Eligible interested patients will be asked to review and sign the Informed consent form, Ver 1.17.22 (attached).

2. Randomization

Subjects will be randomly assigned on the day of screening, or as soon as possible thereafter, to one of two parallel groups: either the treatment (Group Y) or non-treatment group (Group X). Simple randomization will be performed by an individual not involved in screening. The randomizing individual will generate a number from 1 to 100 using randomnumber.org. Randomized participants generating an odd number will be assigned to the treatment group Y; those generating an even number will be assigned to the non-treatment group X.

3. Conditioning Phase, Days 1-14 a. Treatment Group Y

Those individuals assigned to the treatment group will be dispensed medications as outlined below. Medications will be prepared and packaged by a registered hospital pharmacist. These medications will be provided at no cost to the subject. The drugs will be given in the outpatient setting, for a minimum of 10 days, and a maximum of 14 days, prior to a scheduled surgical procedure in which general anesthesia is anticipated. Participating subjects will be given detailed written instructions ("Patient information brochure Group Y", see attached) outlining the dosing regimen they are to follow. This information will be reviewed with the subject in the presence of a study researcher, and signed by the patient. Patients will begin the conditioning protocol 14 days prior to their scheduled surgical event, but as per the screening procedures, patients will be eligible as long as they can complete at least 10 days of the conditioning protocol. Patients will complete medication dosing on the day prior to their elective surgical procedure. They will not take the study drug on the day of surgery. The maximum dose of each study drug will be at therapeutic or sub-therapeutic levels when compared to typical clinical doses of those drugs. Although commercial preparations of the drugs will be used, the patients will be blinded as to the specific identities of the study medications.

If the scheduled surgery date changes after dosing has begun, the patient will cease to participate unless they can still complete the 10-14 day dosing regimen.

Patients will be asked several questions daily, in the form of the brief daily survey (see Case Report Form, Conditioning) and given the option of answering questions via email or by calling a provided phone number. Patients who have not responded by the following day will be called by the investigators. The daily survey is designed to monitor for nausea, vomiting, and other potential side effects, as well as patient compliance with the daily scheduled dose, and reasons for any non-compliance with the dosage schedule. Patients will also be instructed to call the investigator phone number if they experience any problems or concerns. Any patient experiencing intolerable or severe side effects will stop the study drug but continue to be monitored through the study period.

3b. Non Treatment Group X

The non treatment group X will receive a placebo medication to be taken by mouth twice daily. They will receive a copy of the Patient information brochure Group X (attached). They will still complete the brief daily survey, as per the treatment group.

4. Day of Surgery (Day 11-15)

On the day of the surgical procedure, patients will be assigned as per normal St. Vincent surgical scheduling procedures to a member of the St. Vincent Hospital Department of Anesthesia. The assigned anesthesiologist will be aware the patient is enrolled in the study, but will be blind as to the treatment or non-treatment status of the subject. As per the Safety Plan, they will be alerted as to possible side effects and interactions of the study drugs, and instructed to contact the study physicians or study phone number if they have special concerns. If the attending anesthesiologist feels it necessary to provide optimal care of the patient, they will be told the exact treatment status of the patient.

The anesthesiologist will complete basic information (Case Report Form, Day of Surgery, see attached) about anesthetic technique, including:

Pre-operative medications given

Type and length of surgical procedure

Anesthetic technique

- Induction agent
- Maintenance agent
- Opioid given (intraoperatively)__
- Anti-emetics given (and timing)
- Use of neuromuscular blocking agents and reversal drugs
- Use of pain management techniques (eg. intrathecal or epidural narcotics)

The anesthesiologist will be free to use whatever technique he/she deems suitable for general anesthesia, and will have freedom of choice of medications given, including anti nausea medications.

The final section of the Day of Surgery survey is designated for completion by the Post Operative Care unit (PACU) nurse, who will record the presence or absence of nausea, vomiting, or retching, and the administration of any PONV treatment medications from the time the patient is admitted to the PACU until they are discharged, either to home or to inpatient status. The PACU nurse will be blind as to treatment status of the patient.

A separate postop survey (see Case Report Form, Post operative survey) will be completed by a researcher, recording the patient reported incidence of delayed nausea and vomiting and other possible side effects, as well as any pain medications or anti-nausea medicines given in the period 24-72 hours post-operatively, as well as overall satisfaction with the procedure and their postoperative course. This survey will be completed by phone call interview, or in person if the patient is available in hospital.

Risks and Benefits to the Subjects:

Patients may benefit individually if those in the treatment group experience a reduced incidence of post operative nausea and vomiting. There may be a collective benefit to the population of patients receiving general anesthesia if this study can result in strategies to reduce overall incidence of post operative nausea and vomiting.

Although the ultimate purpose of this study is to reduce the chance of having nausea or vomiting after surgery, it is possible that the drugs given may cause mild nausea or vomiting. It is also possible that patients could experience any of the known side effects of these drugs including:

Medication #1, 5-Hydroxytryptophan (5-HTP):

This medication is a naturally occurring substance I the body, which converts tryptophan into 5-HTP. When given in sufficient dosages it can cause nausea, diarrhea, loss of appetite, and an increase in blood pressure. It may cause myalgias, rash, edema or flushing. When given long term, there have been rare reports of heart valve damage. There have also been reports of a condition called eosinophilia-myalgia syndrome, where those taking the medication have muscle tenderness, pain and blood abnormalities. This syndrome may have actually been caused by a contaminant in the medicine, but this is not known for sure.

The FDA has not evaluated 5-HTP as to risk in pregnancy.

Additional background on the safety of 5-HTP is given in the attachment Safety Plan.

Medication #2, Levodopa:

May cause low blood pressure, nausea, confusion, changes in emotions or dreams, and fainting spells. Most side effects result when patients are taking this medication over a longer (months) period of time. Those side effects include involuntary movements and muscle spasm, sleep disturbances, including a hard time getting to sleep and sleepiness during the daytime.

Levodopa may exacerbate peptic ulcer disease, and rarely be associated with neuroleptic malignant syndrome, asterixis, hypokalemia, hyponatremia and cardiac arrhythmias.

Levodopa has not been categorized by the FDA as to pregnancy risk. Some of the levodopa carbidopa combination drugs have been designated Category C.

Additional background on the safety of levodopa is given in the attachment Safety Plan.

Medication #3, Hydrocodone:

Commonly seen side effects include nausea, constipation, drowsiness and euphoria. Effects on breathing can occur, including decreased respiratory rate and worsening of sleep apnea. Other medications could add to the sleepiness effect. They may experience difficulty with urinary voiding, dry throat and rash or pruritis. Taken long term, there could be a risk of addiction or dependence. Patients taking hydrocodone may test positive on a drug or blood tests for pain medications (for instance, a work related drug test) during the 10-14 days they are on the medication, and for several days afterward.

Hydrocodone, as with all narcotic pain medications, can possibly impair mental function and coordination. Although the dosage given in this study is relatively small, it is impossible to know how any individual might react. Therefore, the patient instructions will tell patients to only take the medication at bedtime when they do not plan on driving, operating machinery or making important decisions. There are no hard and fast rules as to the legality of driving with hydrocodone, but drivers who show signs of impairment can be at legal risk.

Hydrocodone is a Category C drug in pregnancy.

Please see special considerations for hydrocodone in the Safety Plan.

General side effects that might be common to one or more of these medications include: Rash, itching, flushing, drowsiness, diarrhea, nausea, decreased appetite, stomach irritation or bleeding, or irregular heartbeat.

Although the drugs to be given are often taken by some patients before or after surgery, it is possible that there might be unknown or unexpected side effects or interactions between these drugs or between these drugs and the prescribed anesthetic drugs, which were not anticipated.

Compensation:

Patients will be given a $50 gift card as compensation on the day of their surgical procedure. Patients whose surgery is cancelled or postponed but who have still participated in the pre-operative phase of the study will be mailed $50 gift certificates.

Patients will be given or mailed a second $50 gift card when they have completed the final survey.

Dosing Protocols:

Treatment Group Y:

Drug #1 (5-Hydroxytryptophan, or 5-HTP), supplied as 50 mg. capsules

Drug #2 (L-3,4-dihydroxyphenylalanine, or levodopa, or L-DOPA), supplied as 50 mg. tablets Drug #3 (hydrocodone), supplied as scored combination tablets containing 5 mg. of hydrocodone and 500 mg. of acetaminophen All drugs administered PO.

The dosing protocols follow:

Days 1-4: AM: One 50 mg. capsule of 5-HTP (Drug #1)
PM: One 50 mg. tablet levodopa (Drug #2)
One half of a scored hydrocodone tablet (2.5 mg. hydrocodone) (Drug #3)

Days 5-8: AM: One 50 mg. capsule of 5-HTP (Drug #1)
One 50 mg. tablet of levodopa (Drug #2)
PM: One 50 mg. capsule of 5-HTP (Drug #1)
One 50 mg. tablet of levodopa (Drug #2)
One half of a scored hydrocodone tablet (Drug #3)

Days 9-12: AM: Two 50 mg. capsule of 5-HTP (Drug #1)
One 50 mg. tablet of levodopa (Drug #2)
PM: One 50 mg. capsule of 5-HTP (Drug #1)
Two 50 mg. tablets of levodopa (Drug #2)

One hydrocodone tablet (5 mg. hydrocodone) (Drug #3)

Days 13-14 AM: Two 50 mg. capsules of 5-HTP (Drug #1)

Two 50 mg. tablets of levodopa (Drug #2)

PM: Two 50 mg. capsules of 5-HTP (Drug #1)

Two 50 mg. tablets of levodopa (Drug #2)

One hydrocodone tablet (Drug #3)

Patients will be instructed to take the AM or PM doses at any convenient time, with or without food, but should attempt to take the daily dose at approximately the same time each day. If patients experience nausea, vomiting, or other side effects in the 24 hour period after a dose, they will drop down to the next lowest dose the following day, or hold a dose if they were already at the lowest dosing level.

Patients will be instructed (see patient instructions) to take Drug #3 (hydrocodone) dosage only after dinner and if there is no chance they will be driving, operating machinery, or performing any activity that will require physical or mental concentration until the following morning. They will be instructed not to drink alcohol, or take any other medications which cause sleepiness after dinnertime. If subjects still feel any residual sleepiness or impairment the following morning, they will be instructed to not drive an automobile until the sleepiness has subsided.

Data will be collected daily by email and phone call as outlined in the Case Report Form, Conditioning phase.

Total drug dispensed:

5-HTP (Drug 1): #32 50 mg. capsules

Levodopa (Drug 2): #32 50 mg. tablets

Hydrocodone (Drug 3): #10 5 mg. hydrocodone/500 mg. acetaminophen tablets

Although commercial preparations of the drugs will be used, the patients will be blinded as to the identities of Drugs #1 and #2. They will be told the identity of Drug#3, hydrocodone, so they can evaluate whether or not they should take the drug, as per the patient instructions. Packaging and labeling of the drugs will be performed by a registered hospital pharmacist.

Non-Treatment Group X:

Subjects in the non-treatment group will receive a placebo medication, also packaged by a licensed hospital pharmacist. They will be instructed to take the medication as per the following schedule:

Day 1-6: One tablet by mouth in the morning, and one tablet by mouth in the evening Day 7-14 Two tablets by mouth in the morning, and two tablets by mouth in the evening As with the treatment group, patients in the non-treatment group will be told to follow the same precautions with the evening dose as if they were actually receiving a narcotic medication.

Statistical Analysis:

The study will continue recruiting participants until 250 (N) total subjects have been enrolled. Raw data will be analyzed by the hospital biostatistician.

The sample size for this study is based on two-sided Type 1 error rate of 5%, and a difference in nausea rates of 0.15, (assuming a nausea rate of 0.3 for the control and 0.15 for the active group) with a statistical power of 80%. Based on these assumptions a sample size of 241 patients will be needed (approximately 120 for the treatment group and 120 for the non treatment group). Fisher's exact tests will be used to test for differences between treatment groups. Nominal logistic regression may also be used to test the impact of covariates on the outcomes.

Patient Selection:

Inclusion Criteria:

Medically healthy, ASA Class I or II, or III patients scheduled for elective abdominal (either laparoscopic or open abdominal) procedures.

Female, 18-65 years old, post-menopausal for greater than 2 years, surgically sterilized or with a negative pregnancy test within 7 days prior to administration of study drugs Male, 18-65 years old Willing to take the study medications as directed, answer daily survey questions, and respond to follow up call post procedure Exclusion Criteria:

Under age 18 or over age 65

Pregnant, potentially pregnant, or breastfeeding mothers.

Patients currently taking any of the study drugs or drugs which act on the same receptor class as the study drugs. These drugs would include opioid or narcotic pain medications, selective serotonin re uptake inhibitors (SSRIs), and dopaminergic drugs.

Known allergy to any of the study drugs.

Significant renal or hepatic disease (effectively excluded by being>ASA Class III).

History of cardiac disease including myocardial infarction and atrial, nodal or ventricular arrhythmias.

Pre-existent nausea or vomiting due to other causes

Funding:

Application for funding through the St. Vincent Foundation has been initiated. Other non-industry foundation funding may be sought at a later date.

Study Definitions:

Nausea will be scored using a 4-point verbal descriptive scale (VDS) (0=no nausea, 1=mild, 2=moderate, 3=severe).

Sleepiness is defined as a patient reporting somnolence greater than typical in an average day.

Data Collection:

Data will be input directly into an Excel spreadsheet. The following data will be collected on all patients.

Patient demographics including:

- Age
- Gender
- Race/ethnicity
- Height
- Weight
- Tobacco use
- Reproductive status Medical history Medications (name and dosage)

Allergies

Primary Outcome

Incidence of the following side effects:

- Nausea
- Vomiting
- Itching/hives
- Sleepiness
- Headaches

[i] Apfel C C, Laara E, Koivuranta M, Greim C A, Roewer N A. Simplified Risk score for predicting postoperative nausea and vomiting: conclusions from cross-validations between two centers. Anesthesiology 1999; 91:693-700.

[ii] Myles P S, Williams D L, Hendrata M, et al. Patient satisfaction after anaesthesia and surgery: results of a prospective survey of 10,811 patients. Br J Anaesth 2000; 84:6-10.

[iii] Macario A, Weinger M, Carney S, Kim A. Which clinical anesthesia outcomes are important to avoid? The perspective of patients. Anesth Analg 1999; 89:652-8.

[iv] Carroll N, Miederhoff P, Cox F, Hirsch J. Costs incurred by outpatient surgical centers in managing postoperative nausea and vomiting. J. Clin. Anesth 1994; 6:364-9.

[v] Chung F, Mezei G. Factors contributing to a prolonged stay after ambulatory surgery. Anesth Analg 1999; 89:1352-9.

[vi] Andrews P L, Davis C J, Bingham S, et al. The abdominal visceral innervation and the emetic reflex: pathways, pharmacology, and plasticity. Can J Physiol Pharmacol 1990; 68:324-345.

[vii] Andrews P L, Sanger G J. Abdominal vagal afferent neurons: an important target for the treatment of gastrointestinal dysfunction. Curr Opin Pharmacol. 2002; 2:650-6.

[viii] Chimbira W, Sweeney B P. The effect of smoking on postoperative nausea and vomiting. Anaesthesia 2000; 55:540-4.

[ix] Whalen F, Sprung J, Burkle C, et al. Recent smoking behavior and postoperative nausea and vomiting. Anesth Analg 2006; 103:70-75.

[x] Sweeney B P, Why does smoking protect against PONV? Br. J. Anaesth. Sweeney 89 (6): 810.

[xi] Kasper S, Fuger J, Moller H J. Comparative efficacy of antidepressants. Drugs. 1992; 43 Suppl 2:11-22; discussion 22-3.

[xii] Apfel C C, Laara E, Koivuranta M, Greim C A, Roewer N A. Simplified Risk score for predicting postoperative nausea and vomiting: conclusions from cross-validations between two centers. Anesthesiology 1999; 91:693-700.

[xiii] Myles P S, Williams D L, Hendrata M, et al. Patient satisfaction after anaesthesia and surgery: results of a prospective survey of 10,811 patients. Br J Anaesth 2000; 84:6-10.

[xiv] Macario A, Weinger M, Carney S, Kim A. Which clinical anesthesia outcomes are important to avoid? The perspective of patients. Anesth Analg 1999; 89:652-8.

[xv] Carroll N, Miederhoff P, Cox F, Hirsch J. Costs incurred by outpatient surgical centers in managing postoperative nausea and vomiting. J. Clin. Anesth 1994; 6:364-9.

[xvi] Chung F, Mezei G. Factors contributing to a prolonged stay after ambulatory surgery. Anesth Analg 1999; 89:1352-9.

[xvii] Lerman J. Surgical and patient factors involved in postoperative nausea and vomiting. Br J Anaesth 1992; 69(Suppl 1):24S-32S.

[xviii] Beattie W S, Lindblad T, Buckley D N, Forrest J B. Menstruation increases the risk of nausea and vomiting after laparoscopy. Anesthesiology 1993; 78:272-6.

[xix] Andrews P L, Davis C J, Bingham S, et al. The abdominal visceral innervation and the emetic reflex: pathways, pharmacology, and plasticity. Can J Physiol Pharmacol 1990; 68:324-345.

[xx] Andrews P L, Sanger G J. Abdominal vagal afferent neurons: an important target for the treatment of gastrointestinal dysfunction. Curr Opin Pharmacol. 2002; 2:650-6.

[xxi] Chimbira W, Sweeney B P. The effect of smoking on postoperative nausea and vomiting. Anaesthesia 2000; 55:540-4.

[xxii] Whalen F, Sprung J, Burkle C, et al. Recent smoking behavior and postoperative nausea and vomiting. Anesth Analg 2006; 103:70-75.

The invention claimed is:

1. A method for reducing post-operative nausea or vomiting in a human patient in need of general anesthesia for surgery, comprising the acts of:

scheduling surgery for the human patient to occur on a future surgery date, said scheduled surgery to include general anesthesia;

administering to the patient one or more series of prescribed medicines during a conditioning phase preceding said general anesthesia;

wherein said one or more series of prescribed medicines includes a dose of a first prescribed medicine selected from the group consisting of serotonergic agonists, selective serotonin reuptake inhibitors, nicotinic acetylcholine receptor agonists, muscarinic receptor agonists, and dopaminergic agonists;

wherein said one or more series of prescribed medicines includes a dose of a second prescribed medicine selected from the group consisting of opioids and analgesics during said conditioning phase;

wherein the act of said administering includes administering dosages of:

(a) 5-hydroxytryptophan, daily, 50 milligrams per day for four days, then 100 milligrams per day for four days, then 150 milligrams per day for four days, then 200 milligrams per day for two days;

(b) levodopa, daily, 50 milligrams per day for four days, then 100 milligrams per day for four days, then 150 milligrams per day for four days, then 200 milligrams per day for two days;

(c) hydrocodone, daily, 2.5 milligrams per day for eight days, then 5 milligrams per day for six days.

* * * * *